United States Patent [19]

Munakata et al.

[11] 4,440,752

[45] Apr. 3, 1984

[54] ANTIBIOTICS Y-16482 α AND/OR Y-16482 β, A PROCESS FOR PRODUCTION THEREOF, AND A PHARMACEUTICAL COMPOSITION CONTAINING EITHER OR BOTH OF THEM

[75] Inventors: Tomohiko Munakata; Katsuyoshi Isagai, both of Nakatsu; Yoshifumi Ikeda, Fukuoka; Junichi Sakai, Nakatsu; Hideo Matsuki, Fukuoka, all of Japan

[73] Assignee: Yoshotomi Pharmaceutical Industries Ltd., Japan

[21] Appl. No.: 355,735

[22] PCT Filed: Jul. 1, 1981

[86] PCT No.: PCT/JP81/00151

§ 371 Date: Feb. 19, 1982

§ 102(e) Date: Feb. 19, 1982

[87] PCT Pub. No.: WO82/00146

PCT Pub. Date: Jan. 21, 1982

[30] Foreign Application Priority Data

Jul. 7, 1980 [JP] Japan .................................. 55-92921

[51] Int. Cl.$^3$ .......................... A61K 35/00; C12P 1/04
[52] U.S. Cl. .................................... 424/118; 424/119; 435/170
[58] Field of Search .................. 424/118, 119; 435/170

*Primary Examiner*—Jerome D. Goldberg
*Attorney, Agent, or Firm*—Berman, Aisenberg & Platt

[57] ABSTRACT

Antibiotics Y-16482 α and/or Y-16482 β, obtained by cultivating a strain belonging to the genus Pseudomonas and capable of producing Y-16482, process of producing either or both of them, and a pharmaceutical composition containing these compounds. Antibiotics Y-16482 α and/or Y-16482 β show an antibacterial activity to gram-positive and gram-negative bacteria and indicate an antitumor activity to experimental tumors.

6 Claims, 4 Drawing Figures

ANTIBIOTICS Y-16482 α AND/OR Y-16482 β, A PROCESS FOR PRODUCTION THEREOF, AND A PHARMACEUTICAL COMPOSITION CONTAINING EITHER OR BOTH OF THEM

TECHNICAL FIELD

The present invention relates to novel antibiotics Y-16482 α and/or Y-16482 β, a process for production thereof, and a pharmaceutical composition containing either or both of them.

DISCLOSURE OF INVENTION

In an attempt of obtaining novel antibiotics, the present inventors, while obtaining many soil microorganisms and isolating antibiotic substances produced by them, came to note that a particular strain belonging to the genus Pseudomonas, when cultivated in a proper medium, accumulated a substance having a strong inhibitory activity against gram-positive as well as gram-negative bacteria and also showing antitumor activity. The isolation and identification of the physicochemical and biological characters of the substance led to the finding that the product was a novel antibiotic and it was named as Antibiotic Y-16482.

Further the present inventors found that Antibiotic Y-16482 consisted of two components, obtained them separately by a purification method as mentioned hereinafter, and named them as Antibiotics Y-16482 α and Y-16482 β, respectively (hereafter may be referred to briefly as Y-16482 α and Y-16482 β, respectively).

The present invention relates to (1) Antibiotics Y-16482 α and/or Y-16482 β and their salts, (2) Process of producing Antibiotics Y-16482 α and/or Y-16482 β, characterized by cultivating a strain belonging to the genus Pseudomonas and capable of producing Antibiotic Y-16482, thereby to cause it to accumulate Antibiotics Y-16482 α and/or Y-16482 β in a medium and recovering them, and (3) a pharmaceutical composition characterized in containing Antibiotics Y-16482 α and/or Y-16482 β as the effective ingredients.

All references to tumors throughout this disclosure are applicable to transplanted tumors.

DETAILED EXPLANATION OF INVENTION

As the antibiotic Y-16482-producing microorganism, any strain may be utilized, which belongs to the genus Pseudomonas and is capable of producing Antibiotics Y-16482 α and/or Y-16482 β. For example, a strain A2-2 of *Pseudomonas fluorescens* (hereinafter may be briefly referred to as A2-2 strain) is applicable, which the present inventors isolated from a soil sample obtained at the foot of Mt. Hikosan, in Soeda-cho, Tagawa-gun, Fukuoka.

The microbiological characters of A2-2 strain are as follows:

1. Morphology

The cell grown in Bouillon broth medium and on Bouillon agar medium showed the following morphology:

(1) Rods with round ends, not curved, $0.8 \times 2$ to $3\mu$, arrangement of cells irregular, no chain formed, mostly occuring singly but some in pairs.
(2) No pleomorphism found.
(3) Motile, multiple polar flagella found by Ieifsons flagella-staining method.
(4) No spore formed.
(5) Gram-negative rods alone found in a gram-staining sample at 24 hrs' incubation at 30° C.
(6) Acid-fast staining negative.

2. Observation of growth on various media (1) Bouillon agar
The colony was minute at the 24 hrs' incubation at 30° C. and at 48 hrs' incubation it grew into 1 to 1.5 mm in diameter, circular in entire, smooth on surface, pale yellow, translucent, wet, a little glistening. No water-solble pigment produced.

(2) Bouillion agar slant
The cells at 24 hrs' incubation at 30° C. grew filiform, pale yellow, translucent, wet, dull glistening.

(3) Bouillon broth
The medium became homogeneously turbidity at 24 hrs' incubation at 30° C. and sedimentation occurred at the bottom of the test tube. No pellicle produced.

(4) Bouillon-gelatin
It grew on the surface and along the upper portion of stab line at incubation at 20° to 21° C., and liquefied in infundibule until the third day and then the liquefaction gradually proceeded in stratiform.

(5) Litmus milk
Peptonization occurred and it became slightly acidic.

3. Physiological characters

| Test items | A2-2 strain | Psedomonas, fluorescens. biotype A |
|---|---|---|
| 1. Reduction of nitrate | − | − |
| 2. Denitrification | − | − |
| 3. MR test | − | − |
| 4. VP test | − | − |
| 5. Production of indole | − | − |
| 6. Production of hydrogen sulfide | | |
|    Upper layer of Kligler medium | − | − |
|    Lead acetate paper | − | − |
| 7. Hydrolysis of starch | − | − |
| 8. Utilization of citrate | | |
|    Simmon's medium | + | + |
|    Christensen's medium | + | + |
| 9. Assimilation of inorganic nitrogen sources | | |
|    Growth in nitrate-glucose medium | + | + |
|    Growth in ammonium nitrate-glucose medium | + | + |
| 10. Production of pigments | + | + |
| 11. Urease | − | + |
| 12. Oxydase | + | + |
| 13. Catalase | + | + |
| 14. Range of growth pH | 5.0–10.0 | 5.0–9.0 |

-continued

|  | A2-2 strain | Psedomonas, fluorescens. biotype A |
|---|---|---|
| temperature 37° C. | − | − |
| 25° C. | + | + |
| 4° C. | + | + |
| 15. Adaptability to oxygen | aerobic | aerobic |
| 16. OF test | oxidation | oxidation |

In the table
+ indicates positive
− indicates negative

17. Acid production from carbohydrates in OF medium

| Carbohydrate | | |
|---|---|---|
| D-Arabinose | − | − |
| L-Arabinose | + | + |
| D-xylose | + | + |
| D-Ribose | + | + |
| Rhamnose | − | + |
| D-Mannose | + | + |
| D-Glucose | + | + |
| D-Fructose | + | + |
| D-Galactose | + | + |
| Maltose | − | + |
| Sucrose | − | + |
| Lactose | − | − |
| Trehalose | + | + |
| Melibiose | + | + |
| Raffinose | − | − |
| Melezitose | − | − |
| Adnitol | + | + |
| Dulcitol | − | − |
| D-Sorbitol | + | + |
| D-Mannitol | + | + |
| Inositol | + | + |
| Glycerin | + | + |
| 3% Ethanol | + | + |
| Inulin | − | − |
| Salicin | − | − |
| Cellobiose | − | − |
| OF basal medium (Difco) | − | − |

In the above Table + indicates acid production and − indicates non-production of acids 4. Other Characters

| Test items | A2-2 strain | Pseudomonas, fluorescens. biotype A |
|---|---|---|
| 1. Oxidation of gluconic acid | + | + |
| 2. Decomposition of esculin | − | − |
| 3. Decomposition of cellulose | − | − |
| 4. Utilization of malonic acid | + | + |
| 5. Decomposition of arginine | + | + |
| 6. Decarboxylation of lysine | − | − |
| 7. Decarboxylation of Ornitine | − | − |
| 8. Deamination of phenylalanine | − | − |
| 9. Coagulase | − | − |
| 10. Haemolysis | − | − |
| 11. Growth in Bouillon broth containing 3% NaCl | + | + |
| 12. Resistance to potassium cyanide | + | + |
| 13. Phosphatase | + | − |
| 14. Decomposition of Tween 80 | − | − |
| 15. Acylamidase | − | − |
| 16. Utilization of acetate | + | + |

In the table + indicates positive and − indicates negative

The comparison of the above characteristics of A2-2 strain with the descriptions in Bergey's Manual of Determinative Bacteriology, the 8th edition (1974) suggested a similarity of A2-2 strain to Pseudomonas fluorescens. The comparison showed the difference, however, from known Pseudomonas fluorescens type (1) in that A2-2 strain produced no acid from maltose, sucrose and rhamnose, (2) in that, whilst known Pseudomonas fluorescens strain possessed no phosphatase activity, A2-2 strain had phosphatase and (3) in that A2-2 strain produced Antibiotic Y-16482.

In conclusion, the characters of A2-2 strain differed in some points, but basically coincided with those of known Pseudomonas fluorescens and therefore A2-2 strain was named as Pseudomonas fluorescens A2-2 strain.

This strain has been deposited since May 1, 1981 as FERM BP-14 based on the Budapest Treaty on the International Recognition of the Deposit of Microorganisms, at Fermentation Research Institute, Agency of Industrial Science & Technology, The Ministry of International Trade and Industry (1-3, Yatabemachi Higashi 1-chome, Tsukuba-gun, Ibaragi, Japan, Postal Code 305), as transferred from the original deposit on June 9, 1980, at the same institute under deposit number Ferm P-5618.

The present strain may be used for the purpose of the present invention, if it undergoes mutation in some physiological or biochemical characteristics, so long as it does not lose the capacity of producing Antibiotics Y-16482 α and/or Y-16482 β. Of course the mutation may occur spontaneously or be artificially induced.

In the process of the present invention, A2-2 strain as mentioned above is cultivated. A2-2 strain, when grown under proper conditions, produces Antibiotics Y-16482 α and Y-16482 β.

The medium to be employed contains carbon sources which the present strain can assimilate, nitrogen sources and inorganic salts which the strain can utilizes. If need be, minor nutrient-promoting substances, minor effective substances such as precursors may be added to the medium.

As examples of carbon sources which A2-2 strain can assimilate, there may be mentioned glucose, mannitol, glycerol, fructose, etc., and as examples of nitrogen sources which the strain utilizes, there may be mentioned organic nitrogen-containing matters such as beef extract, peptone, casein, corn steep liquor, soy bean flour, dry yeast, and inorganic nitrogen-containing compounds such as sodium nitrate, ammonium sulfate, and they are efficiently utilized.

The cultivation may be conducted by inoculating A2-2 strain in a proper medium and incubating under aerobic conditions, preferably at a pH of around neutrality.

The strain can grow at a temperature between 4° and 35° C., but a temperature from 20° to 27° C. is desirable. The period for incubation ranges from 2 to 4 days.

As the means of recovering Antibiotics Y-16482 α and/or Y-16482 β from the cultured medium, any means may be optionally applied, which are usually employable for the harvest of such microbial metabolites. Thus, there may be employed such means as filtration, concentration, exchange chromatography by ion-exchanger, activated carbon, silica gel, absorption chromatography by alumina and a synthesized absorbent (e.g. Amberlite XAD-2, Diaion HP-20), transfering among various solvents, precipitation means, separation of impurities, dialysis, drying, recrystallization, etc., solely or in combination.

Because the present antibiotics are amphoteric and transferable in an organic solvent such as ethyl acetate under a slightly alkaline condition, these physicochemical characters are taken advantage of for the purpose of purification.

Further, as the antibiotics are unstable at a strong alkalinity, it is advantageous to keep the solution slightly alkaline or acidic during the purification process.

By way of example, treatment of the cultured medium is carried out by keeping the pH of the surpernatant solution neutral (pH 7) or slightly acidic (e.g. pH=5) and absorbing it to a synthesized absorbent (Amberlite XAD-2, Diaion HP-20, etc.), thereby to concentrate the objective materials. The absorbent is washed with water and an aqueous solvent (e.g. aqueous methanol, aqueous acetone) for removing impurities. The active substances are separately recovered in a high purity therefrom, if use is made of a gradient elution between organic solvent (methanol, acetone, etc.) and water, or between water of pH 7 to 1 adjusted with hydrochloric acid, etc., as the eluting agent.

Antibiotics Y-16482 α and Y-16482 β of the present invention can be converted into the corresponding acid addition salts, when treated with inorganic acids (hydrochloric acid, hydrobromic acid, nitric acid, phosphoric acid, sulfuric acid, etc.), organic acids (oxalic acid, succinic acid, maleic acid, fumaric acid, p-toluenesulfonic acid, etc.) in the per se conventional manner.

The physicochemical characters of Antibiotic Y-16482 α as its hydrochloride are as follows:

(1) Appearance: pale yellow powder (2) Melting point: it begins to carbonize at 215° C. and to liquefy at 260° C.

(3) Elemental analysis: C 55.10%, H 6.61%, N 8.88%, $Cl^{\ominus}$ 11.40%

(4) Exo-alanyl group exists.

(5) Solubility: soluble in water and methanol, sparingly soluble in ethyl acetate, chloroform, ether and benzene.

(6) Specific rotation:
$[\alpha]_D^{21} - 106°$ (C=0.5, methanol)

Figure 1:
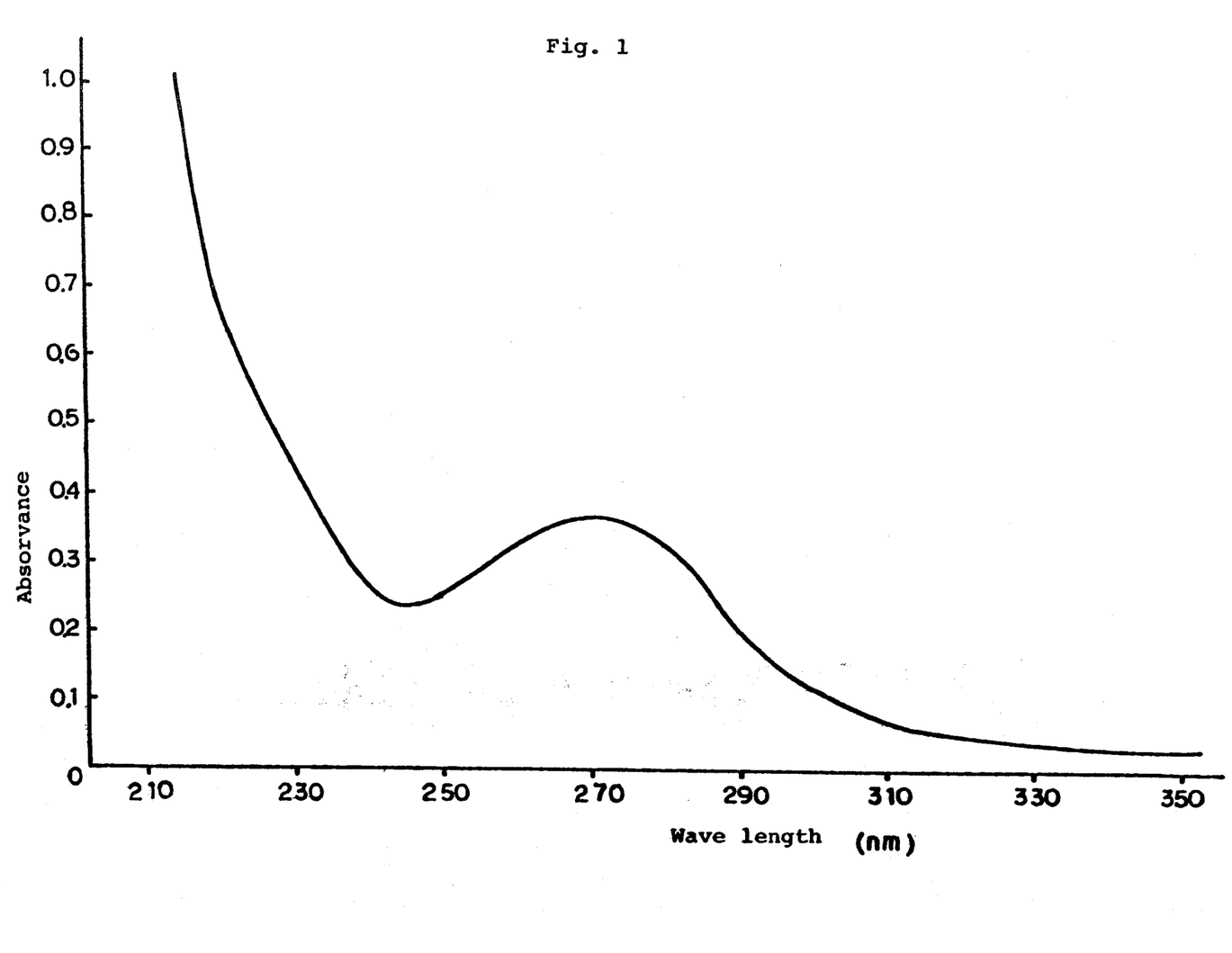
FIG. 1 indicates the ultraviolet absorption spectrum of hydrochloride of Antibiotic Y-16482 α as measured in a methanolic solution (concentration: 25.4 mcg/ml)

(7) Ultraviolet absorption spectrum (concentration: 25.4 mcg/ml, in methanol): λ max=270; nm($E_1\ cm^{1\%}$=145) (See FIG. 1)

Figure 2:
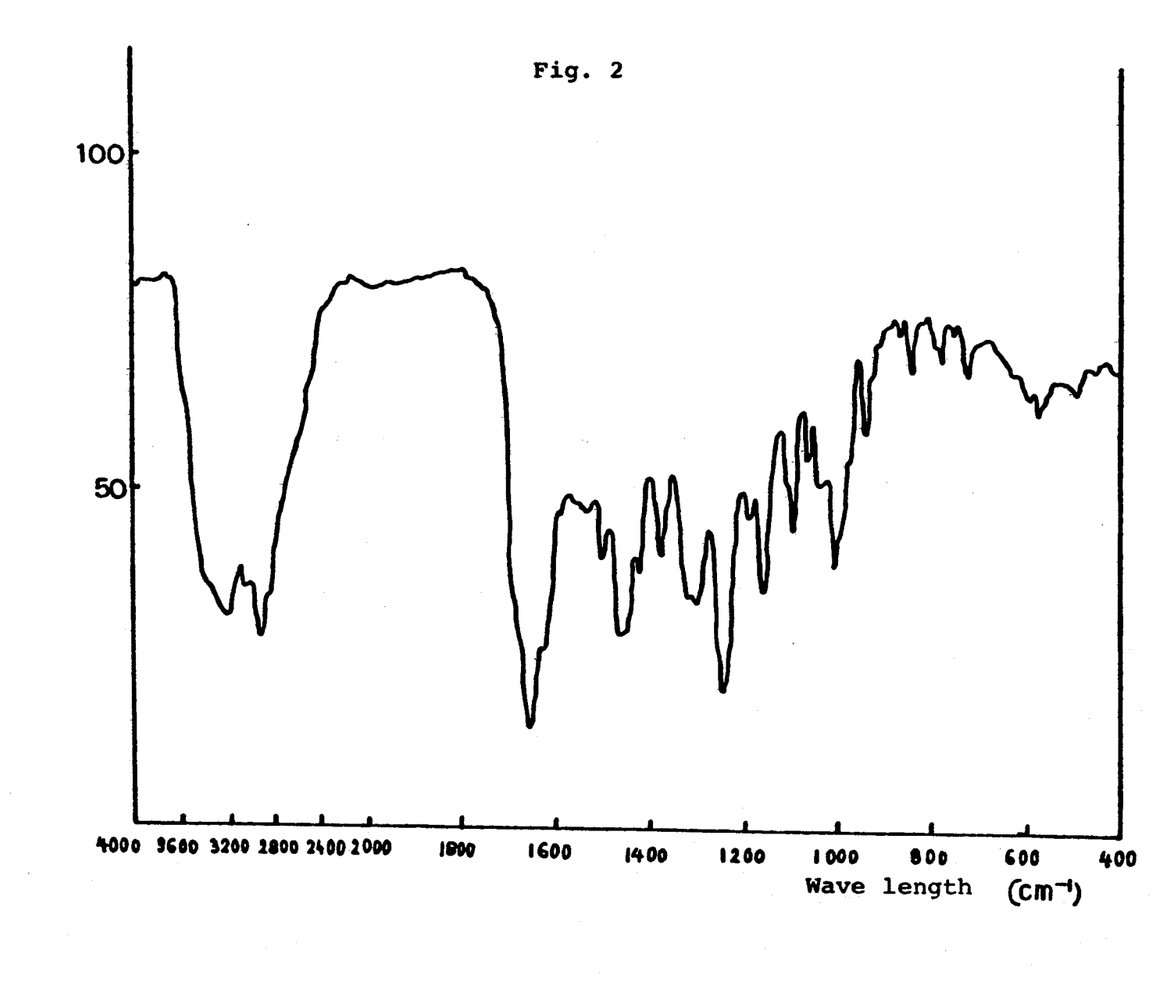
FIG. 2 indicates the infrared absorption spectrum of hydrochloride of Antibiotic Y-16482 α as measured by KBr method.

(8) Infrared absorption spectrum (KBr method): main absorption (cm$^{-1}$) 3200, 2950, 1660, 1460, 1240, 1000 (see FIG. 2)

(9) Thin-layer chromatography (silicagel): Rf=0.6 (toluene: chloroform:methanol=1:3:2); Rf=0.45 (n-butanol:acetic acid:water=4:1:1)

(10) Color reaction: positive to ninhydrin and Dragendorff reaction (11) Alkalinity-Acidity-Neutrality: amphoteric compound The physicochemical characters of Antibiotic Y-16482 β as hydrochloride are as follows:

(1) Appearance: Pale yellow powder (2) Melting point: it begins to carbonize at 230° C. and to liquefy at 300° C. or a higher temperature (3) Elemental analysis: C 54.83%, H 6.54%, N 9.01%, $Cl^{\ominus}$ 11.99%

(4) Molecular weight: peak of molecular ion according to high sensitive mass spectrum is 524.2629±5.7 mmu (5) Molecular formula: $C_{28}H_{36}N_4O_6 \cdot 2HCl \cdot H_2O$ (6) Exo-alanyl group exists.

(7) Solubility: soluble in water and methanol, sparingly soluble in ethyl acetate, chloroform, ether, benzene.

(8) Specific rotation: $[\alpha]_D^{21} - 144°$ (C=0.5, methanol)

Figure 3:
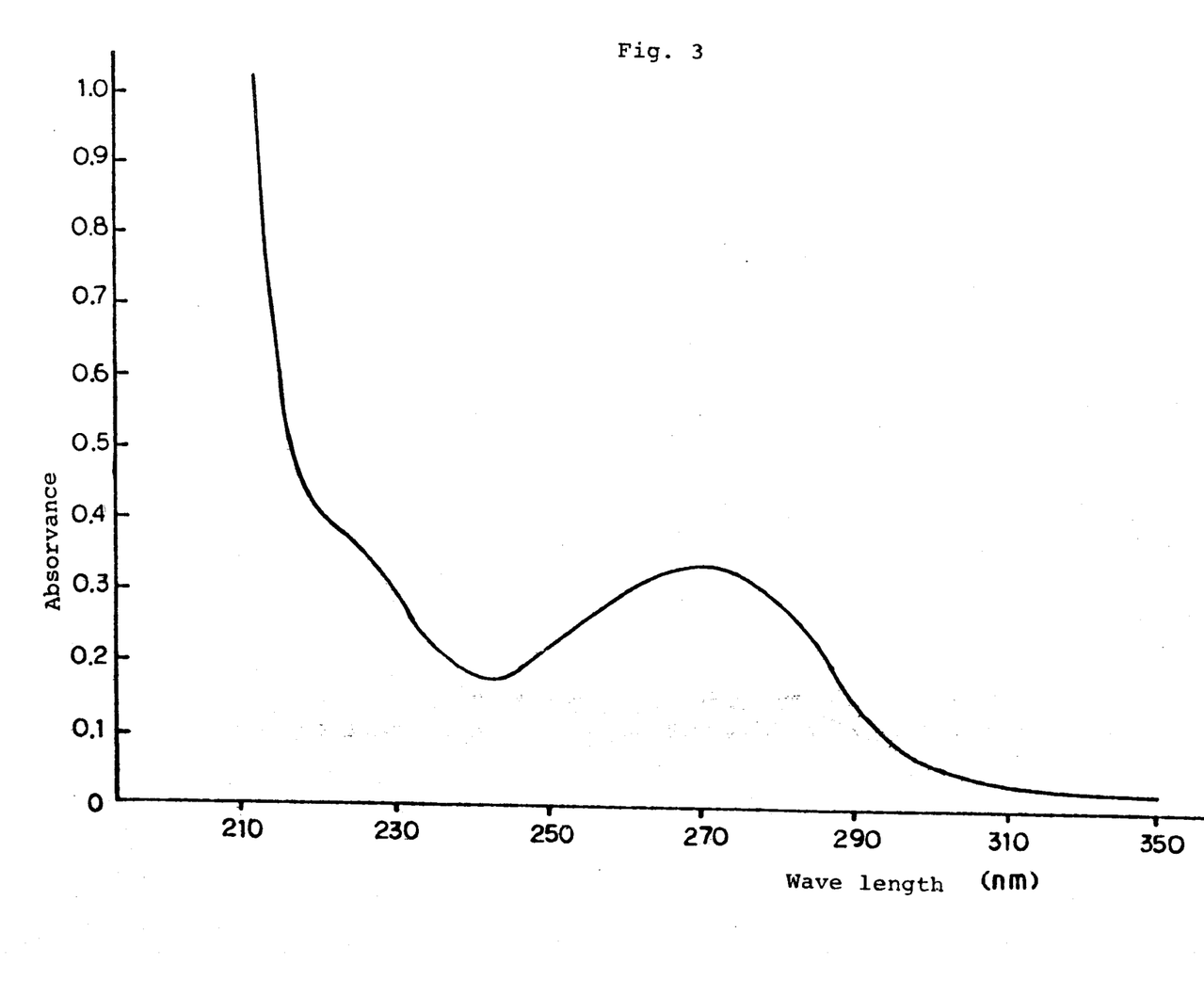
FIG. 3 indicates the ultraviolet absorption spectrum of hydrochloride of Antibiotic Y-16482 β as measured in a methanolic solution (concentration: 20.6 mcg/ml)

(9) Ultraviolet absorption spectrum (in methanol, concentration: 20.6 mcg/ml): λmax=271 nm ($E_1\ cm^{1\%}$=162) (See FIG. 3)

Figure 4:
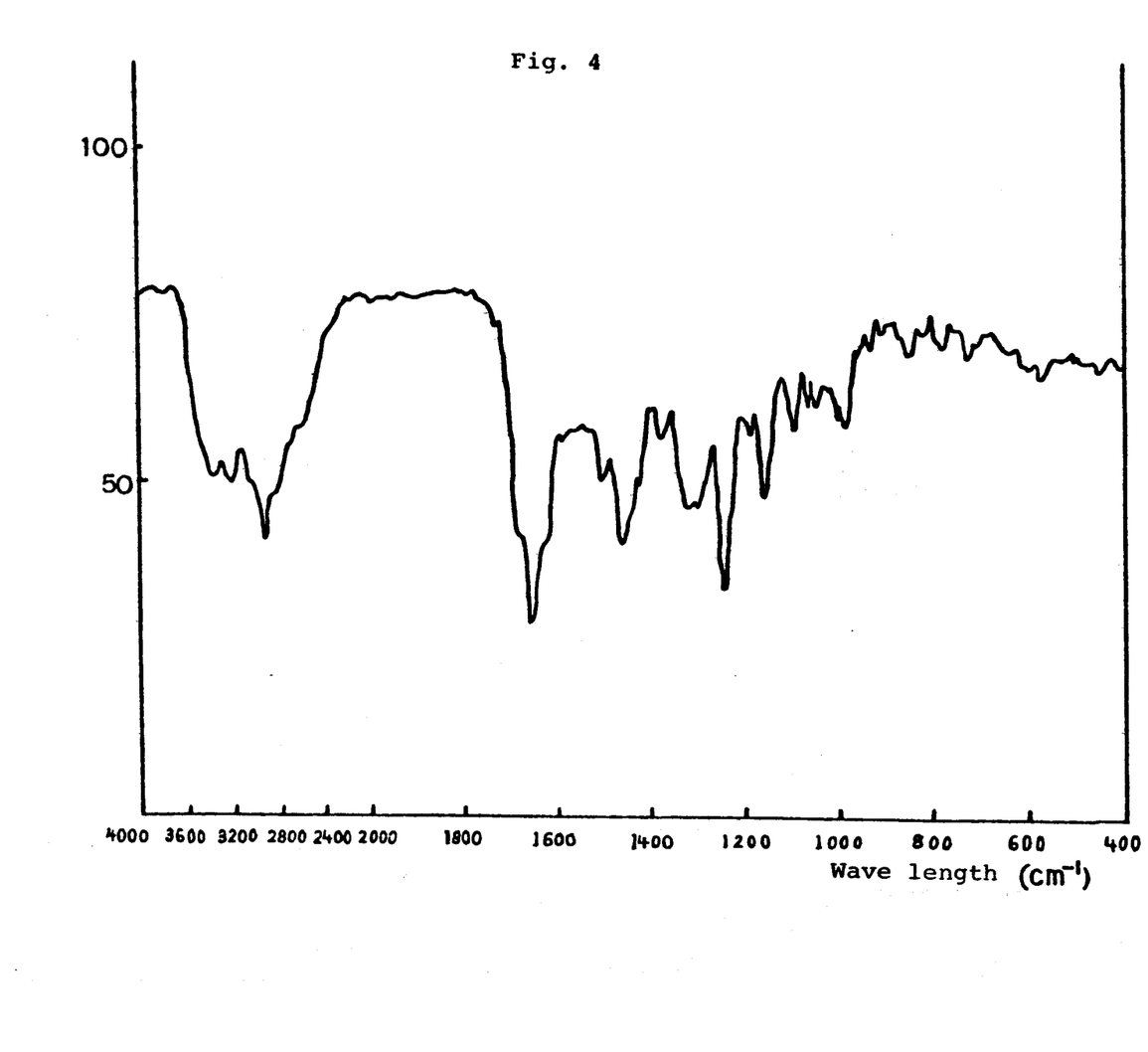
FIG. 4 indicates the infrared absorption spectrum of hydrochloride of Antibiotic Y-16482 β as measured by KBr method.

(10) Infrared absorption spectrum (KBr method): main absorption (cm$^{-1}$) 3350, 3200, 2950, 1660, 1460, 1240 (See FIG. 4)

(11) Thin-layer chromatography (Silica-gel): Rf=0.5 (toluene:chloroform:methanol=1:3:2); Rf=0.4 (n-butanol:acetic acid:water=4:1:1)

(12) Color reaction: positive to ninhydrin, Dragendorff reaction and ferric chloride reaction.

(13) Alkalinity-Acidity-Neutrality: amphoteric compound

The present Antibiotics Y-16482 α and Y-16482 β possess antibacterial activities to bacteria, regardless of gram-positive or gram-negative bacteria as shown in the following Table.

As they also present antitumor activities against experimental tumors, they are useful as antibacterial agents and as antitumor agents for transplanted tumors.

(1) As to antibacterial activity, for example, minimum inhibitory concentration according to the standard method by the Japan Society of Chemotherapy is shown in the Table 1.

TABLE 1

| test organism | minimum inhibitory concentration (mcg/ml) | |
|---|---|---|
| | Y-16482 α | Y-16482 β |
| Staphylococcus aureus 209 P | ≦0.20 | 12.5 |
| Staphylococcus aureus 308A-1 | ≦0.20 | 12.5 |
| Staphylococcus aureus 1840 | 0.39 | 25 |
| Streptococcus pyogenes E-14* | ≦0.20 | 0.39 |
| Streptococcus pyogenus S-8* | ≦0.20 | ≦0.20 |
| Streptococcus viridens America* | ≦0.20 | 1.56 |
| Streptococcus faecium IFO 3128* | 0.39 | 50 |
| Streptococcus pneumoniae I* | ≦0.20 | ≦0.20 |
| Corynebacterium diphtheriae* Tronto | ≦0.20 | 6.25 |
| Bacillus subtilis PCI-219 | ≦0.20 | 12.5 |
| Escherichia coli NIHJ JC-2 | 1.56 | 100 |
| Escherichia coli O-111 | 0.78 | 100 |
| Escherichia coli T-7 | 0.78 | >100 |
| Salmonella typhosa Boxhill-58 | ≦0.20 | 25 |
| Shigella flexneri EW-10 | ≦0.20 | 12.5 |
| Shigella sonnei EW-33 | ≦0.20 | 12.5 |
| Klebsiella pneumoniae DT | 0.20 | 12.5 |
| Proteus vulgaris IFO 3988 | 1.56 | >100 |
| Proteus morganii IFO 3168 | 100 | >100 |
| Proteus mirabilis IFO 3849 | >100 | >100 |
| Pseudomonas aeruginosa U-31 | 25 | >100 |
| Serratia marcescens IFO 12648 | 1.56 | >100 |

As the curture medium, trypsoy agar was employed and * asterisk denotes 10% of horse blood added to the medium.

(2) Antitumor activity

Experiment 1

CDF₁ female mice (in a group of 5 mice, 6 to 7 weeks old) were inoculated intraperitoneally with 10⁶ cells of leukemia P-388/0.2 ml/mouse and after 24 hrs, Antibiotic Y-16482 α dissolved in physiological saline was administered intraperitoneally to tumor-inoculated mice once daily for 5 days and the mean survival days and the prolongation ratio of life were examined. The results are shown in Table 2.

TABLE 2

| Dose (mg/kg/day, i. p.) | Mean survival days (day) | Prolongation ratio of life (%) |
|---|---|---|
| 0.1 | 15/10 | 50.0 |
| 0.25 | 16/10 | 60.0 |
| 0.5 | 18/10 | 80.0 |
| 1.0 | 20/10 | 100.0 |

In Table 2, mean survival days are expressed by T/C wherein T corresponds to the mean survival days of P388-bearing mice administered with the antibiotic and C corresponds to those of control mice (no administration), and prolongation ratio of life was calculated on the base of the equation below.

$$\text{Prolongation ratio of life (\%)} = \frac{T-C}{C} \times 100$$

This equation applies correspondingly to the following Experiment.

Experiment 2

CDF$_1$ female mice (in a group of 5 mice, 6 to 7 weeks old) were inoculated intraperitoneally with 10$^6$ cells/0.2 ml/mouse of IMC mammary carcinoma and after 24 hrs., Antibiotic Y-16482 α dissolved in physiological saline was administered intraperitoneally to tumor-inoculated mice once daily for 4 days and the mean survival days and the prolongation ratio of life were examined. The results are shown in Table 3.

TABLE 3

| Dose (mg/kg/day, i. p.) | Mean survival days (day) | Prolongation ratio of life (%) |
|---|---|---|
| 0.1 | 16/11 | 45.5 |
| 0.25 | 17/11 | 54.5 |
| 0.5 | 23/11 | 109.1 |
| 1.0 | >30/11 | >172.7 |

Experiment 3

In accordance to the method as described in Cancer Chemother. Rep., 3, (1972), CDF$_1$ female mice (in a group of 5 mice, 6 to 7 weeks old) were inoculated intraperitoneally with cells of melanoma and after 24 hrs, Antibiotic Y-16482 α dissolved in physiological saline was administered intraperitoneally to the mice, once daily for 4 days and the mean survival days and the prolongation ratio of life were examined.

The results are shown in Table 4.

TABLE 4

| Dose (mg/kg/day, i. p.) | Mean survival days (day) | Prolongation ratio of life (%) |
|---|---|---|
| 0.1 | 24/18 | 33.3 |
| 0.25 | 25/18 | 38.9 |
| 0.5 | 25/18 | 38.9 |
| 1.0 | 28/18 | 55.6 |

Experiment 4

CDF$_1$ female mice (in a group of 5 mice, 6 to 7 week old) were inoculated intraperitoneally with 10$^6$ cells/0.2 ml/mouse of leukemia L-1210 and after 24 hrs., Antibiotic Y-16482 β dissolved in physiological saline was administered intraperitoneally to the mice, once daily for 4 days and the mean survival days and the prolongation ratio of life were examined.

The results are shown in Table 5.

TABLE 5

| Dose (mg/kg/day, i. p.) | Mean survival days (day) | Prolongation ratio of life (%) |
|---|---|---|
| 2.5 | 9/8 | 12.5 |
| 5.0 | 9/8 | 12.5 |
| 10.0 | 9/8 | 12.5 |
| 25.0 | 10/8 | 25.0 |

Experiment 5

CDF$_1$ female mice (in a group of 5 mice, 6 to 7 weeks old) were inoculated intraperitoneally with 10$^6$ cells/0.2 ml/mouse of IMC mammary carcinoma and after 24 hrs., Antibiotic Y-16482 β dissolved in physiological saline was administered to the mice, once daily for 4 days and the mean survival days and the prolongation ratio of life were examined. The results are shown in Table 6.

TABLE 6

| Dose (mg/kg/day, i. p.) | Mean survival days (day) | Prolongation ratio of life (%) |
|---|---|---|
| 5.0 | 16/11 | 45.5 |
| 10.0 | 19/11 | 72.7 |
| 25.0 | 23/11 | 109.1 |

(3) Acute Toxicity

To JCL-ICR male mice (in a group of 10 mice, 4 weeks old, body weight 200 to 220 g) Antibiotic Y-16482 α or Y-16482 β was administered intraperitoneally or per os and LD$_{50}$ was calculated from the survival ratio after 7 days by prohibit method. The results are shown in Table 7.

TABLE 7

| Antibiotic (method of administration) | LD$_{50}$ (mg/kg) |
|---|---|
| Antibiotic Y-16482 α (i. p.) | 3.54 |
| Antibiotic Y-16482 β (i. p.) | 70.7 |
| Antibiotic Y-16482 β (p. o.) | 445.0 |

As for the administration routes of Antibiotic Y-16482 α and/or Y-16482 β and acid addition salts thereof for the purpose of tumor therapy, any common route in the field may be applied, including subcutaneous or intramuscular injection or if need be, intravenous injection, per os (administration in a form of tablets capsules, granules, syrup, etc.), rectal administration, external application and dropping.

The amount of administration per once may be optionally chosen so that the Antibiotics effectively inhibit the objective tumor, and desirably in the range of about 0.01 to 30 mg/kg body weight, and in case of injection in the range of 0.01 to 10 mg/kg body weight and in the case of per os administration in the range of 0.02 to 20 mg/kg body weight, although the amount may vary according the intended animals, kinds of tumors, administration routes, preparation forms, etc. Frequency of administration may be optionally chosen in the range of once to four times a daily. The amount of administration per day and the administration schedule may be optionally chosen in accordance with animals and kinds of tumors, symptom and desirably in the range of 0.01 to 40 mg/kg body weight for injection, and in the range of 0.02 to 80 mg/kg body weight for per os administration. Antibiotics Y-16482 α and/or Y-16482 β and acid addition salts thereof may be applied in combination with other antitumor agents.

Preparation Example 1

Injection composed of

| Y-16482 α | 0.5 mg |
|---|---|
| Sodium chloride | 9 mg | filled up to whole 1 ml with distilled water for injection use.

This preparation may be used solely or in a mixture with physiological saline or infusion.

Preparation Example 2

A tablet composed of

| | |
|---|---|
| Y-16482 α | 1.0 mg |
| lactose | 45.4 mg |
| starch | 15 mg |
| microcrystalline cellulose | 1.5 mg |
| methyl cellulose | 0.6 mg |
| talc | 3 mg |
| magnesium stearate | 1 mg |

Preparation Example 3

A suppository composed of

| | |
|---|---|
| Y-16482 α | 2.5 mg |
| Witepsol E$_{75}$ | 922 mg |
| Witepsol H$_{15}$ | 553 mg |

(Witepsol is a registered trade name)

Preparation Example 4

A capsule composed of

| | |
|---|---|
| Y-16482 α | 1.0 mg |
| lactose | 69 mg |
| magnesium stearate | 1 mg |

First, Y-16482 α is admixed with lactose in an amount indicated above, compressed into a tablet, ground and then admixed with magnesium stearate. The mixture is filled into a capsule of No. 4 size each in an amount indicated above.

Preparation Example 5

Fine granular preparation composed of as a unit usage

| | |
|---|---|
| Y-16482 α | 1.0 mg |
| lactose | 350 mg |
| starch | 135 mg |
| methyl cellulose | 3 mg |

Preparation Example 6

Injection composed of

| | |
|---|---|
| Y-16482 β | 5.0 mg |
| sodium chloride | 9 mg | filled up to whole 1 ml with distilled water for injection use.

This preparation may be used solely or in a mixture with phsiological saline or infusion.

Preparation Example 7

A tablet composed of

| | |
|---|---|
| Y-16482 β | 10.0 mg |
| lactose | 45.4 mg |
| starch | 15 mg |
| microcrystalline cellulose | 1.5 mg |
| methyl cellulose | 0.6 mg |
| talc | 3 mg |
| magnesium stearate | 1 mg |

Preparation Example 8

A suppository composed of

| | |
|---|---|
| Y-16482 β | 25.0 mg |
| Witepsol E$_{75}$ | 922 mg |
| Witepsol H$_{15}$ | 553 mg |

(Witepsol is a registered trade name)

Preparation Example 9

A capsule composed of

| | |
|---|---|
| Y-16482 β | 10.0 mg |
| lactose | 69 mg |
| magnesium stearate | 1 mg |

First Y-16482 β is mixed with lactose in an amount indicated above, compressed into a tablet, ground and then admixed with magnesium stearate. The mixture is filled into a capsule of No. 4 size each in an amount indicated above.

Preparation Example 10

Fine granular preparation composed of as a unit usage

| | |
|---|---|
| Y-16482 β | 10.0 mg |
| lactose | 350 mg |
| starch | 135 mg |
| methyl cellulose | 3 mg |

The present invention will be more concretely explained in the following examples, but they should not be thought to indicate the scope of the invention.

EXAMPLE 1

Each of a medium (400 ml) adjusted to pH7.0, which was composed of glucose (2%), mannitol (4%), dry yeast (2%), ammonium sufate (1.0%), potassium secondary phosphate (0.02%), potassium chloride (0.4%), and calcium carbonate (precipitated) (0.8%), was poured into Sakaguchi flask of 2 l in capacity and sterilized at 121° C. for 20 minutes under pressure and after cooling, was inoculated with one loopful of a culture of A2-2 strain (FERM BP-14) and the shake cultivation was conducted at 24° to 26° C. with reciprocal frequency of 180 times per minute in 7 cm of reciprocal length.

After 4 days' cultivation, the cultured media of 6 flasks were combined to give 2 l. The media at the end of the cultivation were of the pH from 7.5 to 8.0 and showed activities of 8 to 16 dilution unit/ml according to a paper disc method with *Staphylococcus aureus* as the test organism. Thus obtained cultured medium (2 l) was, after removal of cells by centrifugation, adjusted to pH9.0 with sodium hydroxide (5 normal) and extracted three times with an equal volume of ethyl acetate.

From the extract solution the active components were transferred into 500 ml of hydrochloric acid (pH1), which was further adjusted to pH9 with sodium hydroxide and extracted three times with an equal volume of ethyl acetate. The combined extract solution was washed once with 200 ml of distilled water. To the ethyl acetate extract solution there was added anhydrous sodium sulfate and the whole was dried, filtered and distilled under reduced pressure to remove ethyl acetate (not higher than 30° C.). About 20 mg of yellow powder thus obtained was dissolved in a mixed solvent of toluene-chloroform-methanol (1:3:0.4) and subjected to silica gel column chromatography (Prepackcolumn, size A, Merck, using the same mixed solvent as the developing solvent. The active fractions were combined and dried under reduced pressure to give yellow powder of Y-16482 α (about 4 mg as its base) and yellow powder of Y-16482 β (about 5 mg as its base). These substances are convertible to the corresponding acid addition salts (e.g. hydrochloride) in a conventional method.

EXAMPLE 2

A medium (20 l) adjusted to pH7.0, which was composed of glucose (2%), mannitol (4%), dry yeast (2.0%), ammonium sulfate (1.0%), potassium secondary phosphate (0.02%), potassium chloride (0.4%) and calcium carbonate (precipitated) (0.8%) was poured into a Jar-fermentor with 30 l in capacity and, after sterilization, inoculated with 2% equivalent of a seed culture of A2-2 strain (FERM BP-14) and the cultivation was carried out at 24° to 26° C. for 72 hrs. under aerated shaking (aeration of 15 l per minute, agitation speed of 300 rotation per minute). The cultured medium at the end of the cultivation indicated pH of 7.5 to 7.7 and showed an activity of 8 to 16 dilution unit/ml. according to a paper disc method using Staphylococcus aureus as the test organism.

The cultured medium (20 l) thus obtained was, after removal of cells by centrifugation, adjusted to pH6 with hydrochloric acid, and the active components were absorbed in 2 l of synthesized absorbent (Diaion HP-20) mounted in a column, from which, after washing with 6 l of water, the active components were eluted out with 5 l of a mixed solution of methanol (80%) and hydrochloric acid (pH 2). The eluate was adjusted to pH 3.0 with hydrochloric acid, and after the methanol was distilled off under reduced pressure, the resulting 1 l of aqueous solution was washed three times with an equal volume of ethyl acetate to remove impurities.

The aqueous layer was adjusted to pH 9.0 with an aqueous sodium hydroxide and extracted three times with an equal volume of ethyl acetate. The ethyl acetate layer was contacted with 1 l of hydrochloric acid (pH1) and the above components were transferred into latter, which solution was further adjusted to pH 9.0 with an aqueous sodium hydroxide solution and extracted three times with an equal volume of ethyl acetate. The extract solutions were combined and washed once with 1 l of distilled water, and after adding anhydrous sodium sulfate, dried, filtrated and, the ethyl acetate was distilled off under reduced pressure (not higher than 30° C.). Thus obtained about 180 mg of yellow powder was dissolved in a mixed solvent of toluene-chloroform-methanol (1:3:0.4) and subjected to silica gel column chromatography (Prepacked column, size B, Merck & Co., Inc.) using the same mixed solvent as the developing solvent. The active fractions were combined and dried under reduced pressure, wherein yellow powder of Antibiotics Y-16482 α (about 60 mg as its base) and Y-16482 β (about 50 mg as its base), were obtained respectively.

EXAMPLE 3

The medium (1000 l), composed of glucose (2%), mannitol (4%), dry yeast (2.0%), ammonium sulfate (1.0%), potassium secondary phosphate (0.02%), potassium chloride (0.4%) and calcium carbonate (precipitated) (0.8%), was adjusted to pH 7.0 and incorporated in a fermentor with 1700 l in capacity, and after sterilization, inoculated with seed culture (2%) of A2-2 strain (FERM BP-14) and aerated cultivation under agitation was carried out at 24° to 26° C., for 72 hrs. (aeration of 300 l/minute, agitation of 200 rotation/minute). The cultured medium attained to pH 7.5 to 7.7 at the end and showed an activity of 8 to 16 dilution unit per ml by a paper disc method using Staphylococcus aureus as the test organism. The cultured medium (1,000 l) thus obtained was, after removal of cells by centrifugation, adjusted to pH 6 with concentrated hydrochloric acid, passed through a column filled with 10 l of synthesized absorbent (Diaion HP-20) to absorb the active components thereto. After washing the column with 20 l of water, the active components were eluted with 30 l of a mixed solution of methanol (80%) and hydrochloric acid (pH 2). The eluate was adjusted to pH 3.0 with hydrochloric acid and after distilling off the methanol under reduced pressure, the resultant aqueous solution (5 l) was washed three times with an equal volume of ethyl acetate to remove impurities. The aqueous layer was adjusted to pH 9 with an aqueous sodium hydroxide, and extracted three times with an equal volume of ethyl acetate. From the ethyl acetate layer the active components were extracted into 3 l of an aqueous hydrochloric acid (pH 1). The extract solution was further adjusted to pH 9.0 with an aqueous sodium hydroxide and extracted three times with an equal volume of ethyl acetate, the combined extract solution being washed with 5 l of distilled water. There was added anhydrous sodium sulfate to the ethyl acetate solution, which was dried, filtrated and the ethyl acetate was distilled off under reduced pressure (not higher than 30° C.). About 1 g of yellow powder thus obtained was dissolved in a mixed solvent of toluene-chloroform-methanol (1:3:0.4) and subjected to a silica gel column chromatography (Prepackcolumn, Size C, Merck & Co., Inc.) using the same mixed solvent as the developping solvent. The active fractions were combined and dried under reduced pressure, whereby yellow powder of Antibiotics Y-16482 α (about 400 mg as its base) and Y-16482 β (about 450 mg as its base) were respectively obtained.

What is claimed is:

1. Antibiotic Y-16482 α or Y-16482 β, hydrochloride of which having the following characters;
   (I) Antibiotic Y-16482 α, hydrochloride of which having the following characters:
      (1) Appearance: pale yellow powder
      (2) Melting point: it begins to carbonize at 215° C. and to liquefy at 260° C.
      (3) Elemental analysis: C 55.10%, H 6.61%, N 8.88% Cl$^{\ominus}$ 11.40%
      (4) Exo-alanyl group exists
      (5) Solubility: soluble in water, methanol, sparingly soluble in chloroform, ether and benzene.
      (6) Specific rotation: $[\alpha]_D^{21} - 106°$ (c=0.5, methanol)
      (7) Ultraviolet absorption spectrum (concentration: 25.4 mc g/ml. in methanol): λmax=270 nm ($E_1\ cm^{1\%}$=145) (See FIG. 1)

(8) Infrared absorption spectrum (KBr method): main absorption (cm$^{-1}$) 3200, 2950, 1660, 1460, 1246, 1000 (See FIG. 2)

(9) Thin-layer chromatography (silica gel): Rf=0.6 (toluene:chloroform:methanol=1:3:2), Rf=0.45 (n-butanol:acetic acid:water=4:1:1)

(10) Color reaction: positive to ninhydrin and Dragendorff reaction (11) Alkalinity-Acidity-Neutrality: amphoteric compound or (II) Antibiotic Y-16482 β, hydrochloride of which having the following characters:

(1) Appearance: pale yellow powder (2) Melting point: it begins to carbonize at 230° C. and to liquefy at 300° C. or a higher temperature (3) Elemental analysis: C 54.83%, H 6.54%, N 9.01%, Cl$^{\ominus}$ 11.99%

(4) Molecular weight: peak of molecular ion according to high sensitive mass spectrum is 524.2629±5.7 mmu.

(5) Molecular formula: $C_{28}H_{36}N_4O_6 \cdot 2HCl \cdot H_2O$ (6) Exo-alanyl group exists.

(7) Solubility: soluble in water and methanol, sparingly soluble in ethyl acetate, chloroform, ether and benzene.

(8) Specific rotation: $[\alpha]_D^{21} -144°$ (c=0.5, methanol)

(9) Ultraviolet absorption spectrum (in methanol, concentration 20.6 mcg/ml); max=271 nm ($E_1$ $cm^{1\%}$=162) (See FIG. 3)

(10) Infrared absorption spectrum (KBr method): main absorption (cm$^{-1}$) 3350, 3200, 2950, 1660, 1460, 1240 (See FIG. 4)

(11) Thin-layer chromatography (silica gel): Rf=0.5 (toluene:chloroform:methanol=1:3:2), Rf=0.4 (n-butanol:acetic acid:water=4:1:1)

(12) Color reaction: positive to ninhydrin, Dragendorff reaction (13) Alkalinity-Acidity-Neutrality: amphoteric compound 2. Antibiotic Y-16482 α as defined in claim 1.

3. Antibiotic Y-16482 β as defined in claim 1.

4. A pharmaceutical composition containing an antibiotic-effective amount of a compound defined in claim 1, 2 or 3 and a pharmaceutically acceptable carrier or diluting agent.

5. A process of producing Antibiotics Y-16482 α and/or Y-16482 β, characterized by cultivating a strain, A2-2 of *Pseudomonas fluorescens*, FERM BP-14, capable of producing Antibiotic Y-16482, thereby causing it to accumulate Antibiotics Y-16482 α and/or Y-16482 β in a medium and recovering either or both of them.

6. A process according to claim 5 of producing, accumulating and recovering Antibiotic Y-16482 α.

* * * * *